United States Patent [19]

Kral

[11] Patent Number: 5,583,144

[45] Date of Patent: Dec. 10, 1996

[54] METHODS FOR TREATING ERECTILE IMPOTENCE

[76] Inventor: John G. Kral, 23 Prospect Ave., Larchmont, N.Y. 10538

[21] Appl. No.: 394,236

[22] Filed: Feb. 24, 1995

[51] Int. Cl.$^6$ .................. A61K 31/445; A61K 31/47; A61K 31/557

[52] U.S. Cl. .................. 514/321; 514/307; 514/573

[58] Field of Search .................. 514/321, 307, 514/573

[56] References Cited

U.S. PATENT DOCUMENTS

| | | | |
|---|---|---|---|
| 2,056,046 | 9/1936 | Fourneau | 260/54 |
| 4,127,118 | 11/1978 | Latorre | 128/79 |
| 5,145,852 | 9/1992 | Virag | 514/253 |
| 5,236,904 | 8/1993 | Gerstenberg et al. | 514/12 |
| 5,242,391 | 9/1993 | Place et al. | 604/60 |
| 5,256,652 | 10/1993 | El-Rashidy | 514/58 |
| 5,270,323 | 12/1993 | Milne, Jr. et al. | 514/309 |
| 5,336,678 | 8/1994 | Cavallini | 514/275 |
| 5,399,581 | 3/1995 | Laragh | 514/396 |
| 5,451,609 | 9/1995 | Bellamy et al. | 514/651 |

OTHER PUBLICATIONS

Morales, et al., Is Yohimbine Effective in the Treatment of Organic Impotence? Results of a Controlled Trial, the Journal of Urology 137: 1168–1172 (1987).

Shabsigh et al., Evaluation of Erectile Impotence, Urology 32: 83–90 (1988).

Juenemann, et al., Hemodynamics of Papaverine and Phentolamine-induced Penile Erection, The Journal of Urology 136: 158–161 (1986).

Levine et al., Side-effects of Self-administration of Intracavernous Papaverine and Phentolamine for the Treatment of Impotence, The Journal of Urology 141: 54–57 (1989).

Stackl et al., Intracavernous Injection of Prostaglandin E1 in Impotent Men, the Journal of Urology 140: 66–68 (1988).

Schramek et al., Dose-dependent Effect and Side Effect of Prostaglandin E1 in Erectile Dysfunction, The British Journal of Clinical Pharmacology 38: 567–571 (1989).

Lee et al., Prostaglandin E1 versus Phentolamine/Papaverine for the Treatment of Erectile Impotence: A Double-blind Comparison, The Journal of Urology 141: 549–550 (1989).

Stief et al., Preliminary Results with the Nitric Oxide Donor Linsidomine Chlorhydrate in the Treatment of Human Erectile Dysfunction, The Journal of Urology 148: 1437–1440 (1992).

De Tejada et al., Pathophysiology of Prolonged Penile Erection Associated with Trazodone Use, the Journal of Urology 145: 60–64 (1991).

Halsted et al., Papaverine-induced Priapism: 2 Case Reports, The Journal of Urology 136: 109 (1986).

Brindley, G. S., Pilot Experiments on the Actions of Drugs Injected Into the Human Corpus Cavernosum Penis, British Journal of Pharmacology 87: 495–500 (1987).

Azadzoi et al., Effects of Intracavernosal Trazodone Hydrochloride: Animal and Human Studies, The Journal of Urology 144:1277–1282 (1990).

Perrone et al., Napamezole, an Alpha-2 Adrenergic Receptor Antagonist and Monoamine Uptake Inhibitor In Vitro, the Journal of Pharmacology and Experimental Therapeutics 254: 471–475 (1990).

Hsu et al, *Chemical Abstracts*, vol. 102, No. 5, 1985, abstract #41265h, p. 177.

*Primary Examiner*—Marianne M. Cintins
*Assistant Examiner*—William R. A. Jarvis
*Attorney, Agent, or Firm*—Gregory Ferraro

[57] ABSTRACT

The present invention relates to methods of relieving erectile impotence in a human male. The method comprises administering to the male an erectile impotence relieving amount of piperoxan and the compositions include an erectile impotence relieving amount of piperoxan or the pharmaceutically acceptable acid addition salts thereof optionally in combination with a pharmaceutically acceptable carrier.

11 Claims, 1 Drawing Sheet

METHODS FOR TREATING ERECTILE IMPOTENCE

FIELD OF THE INVENTION

The present invention relates to compositions and methods for treating male erectile impotence and more particularly to pharmaceutical compositions comprising erection enhancing compounds and methods of their use for the treatment of human erectile impotence.

BACKGROUND OF THE INVENTION

Impotence is the inability to obtain and sustain an erection sufficient for intercourse. Erection is achieved as a result of arterial inflow into the corpus cavernosum of the penis, which produces engorgement of the corpus cavernosum, and subsequent penile erection. According to a 1993 National Institutes of Health Consensus Panel, it is estimated that as many as 30 million American men experience some degree of erectile dysfunction, the prevalence of which increases with age (NIH Consensus Statement, Vol 10(4): 1–31, (1992)). Fifteen to twenty-five percent of all men 65 years and older suffer from some sort of erectile dysfunction, but the disease is also experienced by as many as five percent of men age 40 years. Half of diabetic men exhibit erectile dysfunction. An increased prevalence of the disease is also associated with hypogonadism, hypertension, high blood cholesterol, drugs, neurogenic disorders, Peyronie's disease, priapism, depression, and renal failure (NIH Consensus Statement, Vol 10(4):1–31, (1992)).

Erectile dysfunction affects men of all races and socio-economic backgrounds, but little is known concerning its prevalence according to membership in these groups. Reports indicate that the disease is experienced throughout the world.

The causes of impotence are usually divided into two subcategories a) organic and b) psychological. The organic aspects of impotence are caused by underlying vascular disease such as that associated with hypertension, diabetes mellitus, and prescription medications. Conservative estimates indicate that half of all cases of impotence are of vascular origin. Because the physiologic process of erection is initiated by an increase in blood flow through the penile arteries and shunting of blood into the vascular spaces of the corpus cavernosum, erectile dysfunction can result from vasculogenic disorders. Since erection necessarily involves vasodilation of the arteries of the penis, the pathophysiologic basis of impotence can be contributed to the inability of the arteries of the penis to vasodilate, thereby inhibiting the flow of blood into the erectile tissue.

Agents which produce vasodilation either by directly causing vasodilation or indirectly affecting secondary pathways that produce vasodilation have been described, and are currently being used for the treatment of impotence. Among those agents there are included papaverine (J. Urol. 136: 158–161, 1986), phentolamine (J. Urol. 141: 54–57, 1989), prostaglandin E1 (J. Urol. 140: 66–68, 1988; Br. J. Clin. Pharm. 38: 567–571, 1989; J. Urol. 141: 549–550, 1989), linsidomine chlorhydrate (J. Urol. 148: 1437–1440, 1992), yohimbine (J. Urol. 137: 1168–1172, 1987), and trazodone (J. Urol. 145: 60–64, 1991), which have all been used to produce erection in impotent men.

However, these agents induce erection through a vasodilatory mechanism and often exhibit unwanted side-effects. One of the more common side-effects associated with the use of vasodilators for the induction of erection is priapism, a painful erection of exceeding long duration which may result in fibrosis of cavernosal sinusoidal tissue. Examples of specific vasodilating agents causing priapism or extremely long erections following treatment for erectile dysfunction include papaverine (J. Urol. 136: 109, 1986), phentolamine (Br. J. Pharmacol. 87: 495–500, 1987), phenoxybenzamine (Br. J. Pharmacol. 87: 495–500, 1987), and trazodone (J. Urol. 145: 60–64, 1991).

Thus, there is a still a need for an improved treatment of impotence which does not subject an impotent male to the side-effects of known treatments such as the pain associated with erections of extremely long duration and priapism.

Accordingly, it is a primary object of the present invention to provide a method of treating impotence which avoids any undue side effects such as erections of extremely long duration, and the unwanted side-effects such as pain and need for reversal using other agents.

It is another object of the present invention to provide pharmaceutical compositions comprising piperoxan which compositions are effective for the treatment of human male erectile impotence.

It is another object of the present invention to provide a method of treating impotence using piperoxan.

It is yet another object of the present invention to provide pharmaceutical compositions which are safe, effective, and easy to formulate.

Other features and advantages of the present invention will be apparent to those of skill in the art from the following detailed description and appended claims.

SUMMARY OF THE INVENTION

In accordance with the above-mentioned objectives and others, the present invention is directed to a method of treating erectile impotence in a human male. The method comprises administering to a human male an erectile impotence relieving amount of piperoxan or the pharmaceutically acceptable acid addition salts thereof. The present invention is also directed to pharmaceutical compositions comprising piperoxan and a pharmaceutically acceptable carrier for administration in accordance with such methods.

In a preferred embodiment, piperoxan is administered to a human male in an amount between 0.1 mg/dose and 50.0 mg/dose at a time immediately preceding sexual engagement. Piperoxan is preferably administered through intracavernosal injection or intraurethral delivery.

BRIEF DESCRIPTION OF THE DRAWINGS

The following drawings are illustrative of embodiments of the invention and are not meant to limit the scope of the invention as encompassed by the claims.

DETAILED DESCRIPTION OF THE PREFERRED EMBODIMENTS

Figure 1:
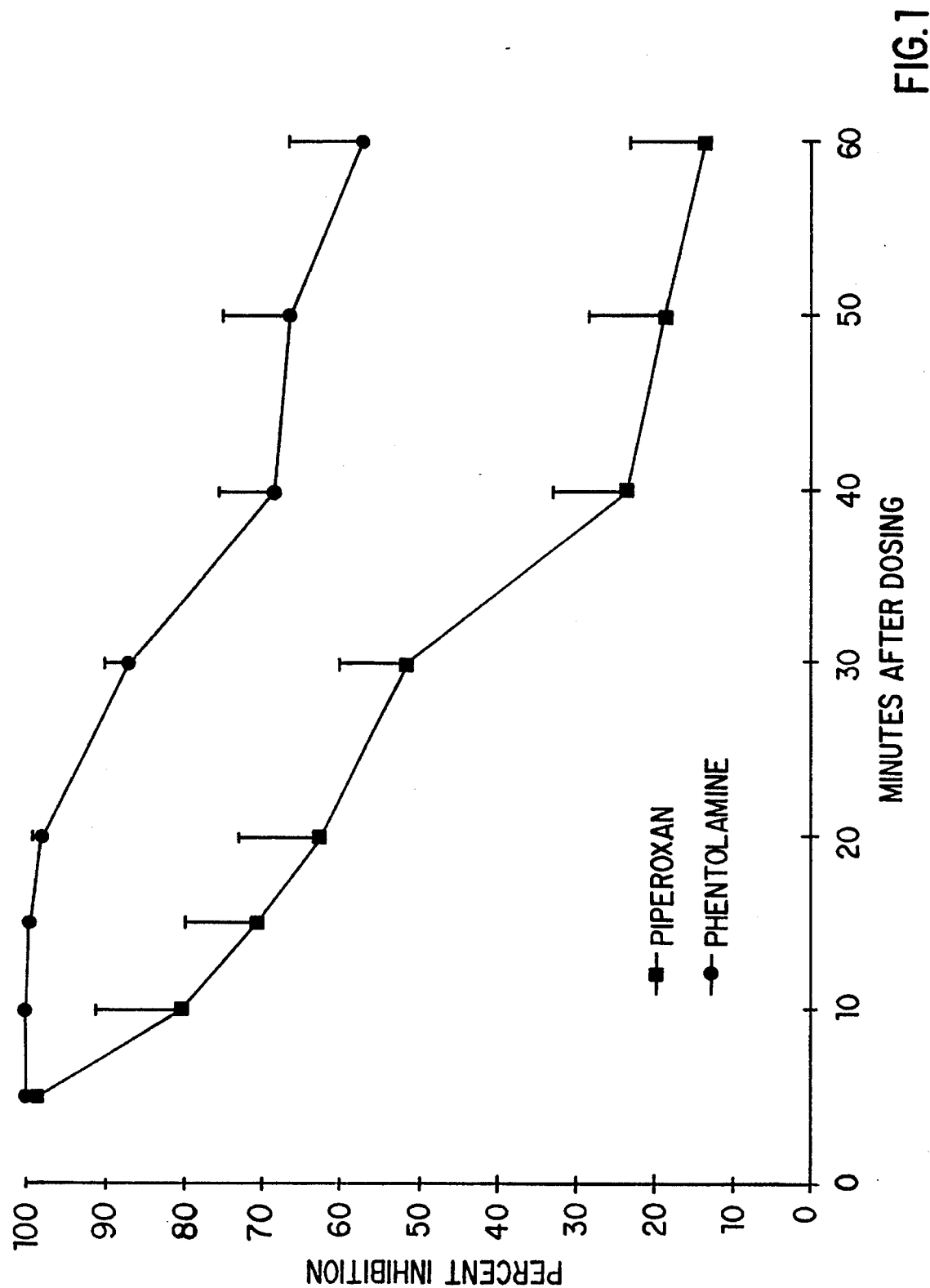
FIG. 1 is a graph illustrating the inhibitor effects of piperoxan, administered in a dose of 0.25 mg/kg iv, as compared to phentolamine, administered in a dose of 0.25 mg/kg iv, on epinephrine induced blood pressure increases in pentobarbital anesthetized rats. Four rats were utilized each for the piperoxan treatment and the phentolamine treatment. The results indicate that the pharmacological action of piperoxan as an alpha-adrenergic antagonist, and, therefore an erection enhancing compound, has a duration of action which is approximately one-half that of phentolamine.

Piperoxan has the chemical structure:

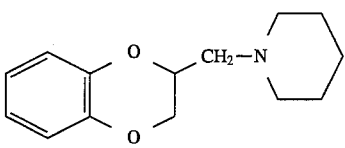

and its pharmaceutically acceptable acid addition salts are described in U.S. Pat. No. 2,056,046, the disclosure of which is hereby incorporated by reference. Piperoxan is known in the literature as 1-[2,3-dihydro-1,4-benzodioxin-2-yl)methyl]piperidine, and 2-piperidinomethyl-1,4-benzodioxan, and 2-(1-piperidylmethyl)-1,4-benzodioxan, and benzodioxane, and benodaine. It has the chemical formula $C_{14}H_{19}NO_2$ and has a molecular weight of 233.30.

Although the name piperoxan represents the free base, the present invention is also meant to embrace the pharmaceutically acceptable acid addition salts, such as hydrochloride, hydrobromide, hydroiodide, nitrate, sulfate, bisulfate, phosphate, acid phosphate, acetate, lactate, citrate, acid citrate, tartrate, bitartrate, salicylate, succinate, maleate, gluconate, methane sulfate, ethane sulfate, methane sulfonate (mesylate), benzenesulfonate (besylate), toluene sulfonate, and p-toluenesulfonate salts. However, preferred is the hydrochloride salt. Any reference to piperoxan throughout is meant to include piperoxan in the free base form and its pharmaceutically acceptable acid addition salts and associated structures such as racemic mixtures and chemically pure D and L isomers.

Anatomically, the human male penis is composed of erectile tissue called the corpus cavernosum and corpus spongiosum. The corpus cavernosum is comprised of two segments, each located adjacent to the urethra. The corpus spongiosum is composed of large venous sinuses which contain relatively little blood when the penis is in the flaccid, relaxed state, but which become very dilated when engorged by blood. The dilation of these tissues contributes directly to penile erection.

Under normal circumstances, erection is initiated by nervous system stimuli. A substantial increase in the inflow of blood to the erectile tissue is facilitated by dilatation of the arteries of the penis as a result of either local or central nervous system stimuli. The nervous stimulation induces vasodilation of the profunda and dorsal arteries of the penis through which the primary erectile tissues of the penis, the corpus cavernosum, receive blood. Increased blood flow to the penis causes engorgement of the erectile tissue, resulting in penile erection. The male erection is therefore a vascular event initiated by neuronal action. The nerves innervating the penis which cause erection are of parasympathetic origin, and stimulation of these nerves results in relaxation of smooth muscle of the arteries of the erectile tissue, with subsequent increased blood flow.

The inability of the arteries of the erectile tissue of the penis to adequately vasodilate will cause erectile dysfunction. This organic basis of impotence has been estimated to be the cause of as much as eighty percent of all impotence. Administration of an appropriate compound which will dilate the profunda and dorsal arteries, allowing increased blood flow to the corpus cavernosum, will produce an erection similar to that which occurs as a result of parasympathetic nervous stimuli. The physiologic basis of this drug-induced erection is the action of vasodilating agents in producing increased blood flow into the penis through the appropriate arteries, engorgement of the corpus cavernosum, and partial constriction of the exiting veins, with the result being a sustainable erection.

The compound of the present invention, piperoxan, when administered appropriately to a human male, blocks the alpha-adrenergic receptors of the arteries of the penis, pharmacologically producing the same effect that under normal circumstances is achieved by parasympathetic nerve stimuli. The central nervous system is composed of sympathetic and parasympathetic nerves, each of which uses specific chemicals for effecting signal transduction across the neuromuscular junction. Adrenergic nerves release chemicals which bind to membrane receptors on muscle cells, the receptors being classified as either alpha or beta subtypes. Alpha-adrenergic receptor antagonism causes relaxation of the arteries of the penis, which normally remain contracted in the flaccid state due to sympathetic adrenergic nerve stimulation (Urology 24: 347–352, 1984). Blockade of adrenergic receptors with specific chemical antagonists results in relaxation of these penile arteries, increased blood flow and subsequent erection.

Piperoxan has various known abilities such as having an antihypertensive effect and being useful as a diagnostic aid for detecting pheochromocytoma. Piperoxan is freely soluble in water and acid solutions, crystals of piperoxan are not hygroscopic and are stable to light, air, and normal storage temperatures, and an aqueous solution of piperoxan at pH 5.0 is stable to autoclaving and to many months of storage at room temperature. However, prior to the present invention, the use of piperoxan as an erection enhancing compound was not known.

As stated, many alpha-adrenergic blocking agents, among other types of nonhormonal compounds, have been used or tested for treating erectile impotence. However, the present invention departs from the prior art in the recognition that piperoxan is shorter acting than the other alpha-adrenergic blocking agents which have been used for the treatment of impotence. The other adrenergic blocking agents used to treat impotence, for example, phentolamine and yohimbine, have an extremely long duration of action, resulting in erections which last several hours, causing pain and general discomfort. Piperoxan, as shown in Example 1, has a pharmacological action which is approximately half that of phentolamine in terms of the duration of vasodilation.

Any method of administration of the above compound found effective in relieving male erectile impotence may be employed. Administration is by intracavernosal injection or intraurethral delivery by a catheter or similar device. Other methods of application may be used as well, including transdermal formulations.

Preferably, the piperoxan compounds of the present invention are employed in combination with a suitable pharmaceutical carrier prior to administration. Such compositions comprise a therapeutically effective amount of piperoxan and a pharmaceutically acceptable carrier or excipient. Such compositions are prepared depending on the nature of administration. Thus, for example, when administration is by injection, an aqueous solution acceptable by intracavernosal injection into the penis is prepared. In this instance, the carriers include but are not limited to water, saline, buffered saline, salts, dextrose, glycerol, and ethanol either alone or in combination. The pharmaceutical compositions will preferably be sterile at the time of administration. Also, a non-irritant preservative may be added to the compositions such as, for example, benzalkonium chloride at 0.05% (w/v) to 0.2% (w/v).

Preferably, a single dose of a pharmaceutical composition in a method of the invention has a volume between about 0.1 ml and about 5 ml, and preferably about 0.5 ml. An erection is induced by a single dose of a composition of the invention.

In the case of intraurethral, transdermal or topical administration, the pharmaceutical carrier includes but is not limited to gels such as petroleum gels, ointments, creams, solutions, sprays, powders, foams and liposome formulations. The carrier is water-soluble, non-irritating, and does not sensitize the skin. In a preferred embodiment, the carrier for this type of administration has a semi-soft, cream-like consistency. This can be obtained by the use of a hydrogel such as hydroxypropylmethylcellulose. A suitable methylcellulose is Methocell E4M which is available from Dow Chemical, Inc. Alternatively, an acrylic acid polymer can be used to obtain a topical vehicle of the desired consistency. Carbopol 934P, commercially available from B. F. Goodrich Co., when neutralized, is a suitable acrylic acid polymer for this purpose. The weight percent of the polymer in the composition is in the range of about 0.1 to about 5.

The pharmaceutical compositions comprising piperoxan may optionally also comprise other active agents which enhance or complement the erection enhancing effects of piperoxan. Such compounds include, but are not limited to, prostanglandins, for example, prostaglandin $E_2$ and direct vasodilators, for example, papaverine. These compounds merely supplement the direct action of piperoxan in producing the erection enhancing effects.

Preferably, piperoxan is administered according to one of following methods. Piperoxan may be administered by injection wherein piperoxan is dissolved in saline at a concentration ranging from 0.25 to 50 mg/ml. This solution is placed into a syringe attached to a 27 gauge, 0.5 inch needle. A volume of 0.5 ml is injected intracavernosally. In another example of a preferred method of use, piperoxan is formulated in a petrolatum gel, which is then applied externally to an intraurethral catheter. The dosage of piperoxan is in the range of 1 to 10 percent of the weight of gel applied. The catheter is inserted into the urethra, and piperoxan is administered intraurethrally to produce the vasodilation required for erection.

Any amount of the above described compounds may be administered by injection which is effective in relieving human male erectile impotence. A range of about 0.5 mg/dose to 50 mg/dose is used in a single dose. Preferably about 5 mg/dose to about 25 mg/dose is used in a single dose.

The following examples are specific embodiments of the present invention and are given to further illustrate the invention and are not meant to limit the scope of the invention as encompassed by the claims.

EXAMPLE 1

Eight male normotensive Sprague-Dawley rats weighing between 350 to 380 grams were used in these studies. Animals were fed and watered ad libitum in a temperature (22 degrees and humidity (50%) controlled vivarium with a light dark cycle of 12 hours.

Drug Preparation:

Epinephrine, D,L-piperoxan, and phentolamine (Sigma Chemical Company; St. Louis, Mo.) were solubilized in 0.9% saline on the day of the experiment. All doses were calculated on free base weight. The rats were anesthetized with pentobarbital sodium 60 mg/kg i.p. All animals were checked for depth of anesthesia before proceeding further using the corneal reflex and toe pinch response as indicators. The ventral surface of the neck was shaven and a longitudinal incision, approximately 2 cm long, was made on the ventral surface. The trachea was isolated and intubated (PE205; Intramedic, Parsippany, N.J.). The left internal jugular vein and right common carotid artery were cannulated (PE50; Clay Adams, Becton Dickinson, Parsippany, N.J.). The cannulas were heparinized (Sodium heparin 60 units/ml) and inserted approximately 1.5 cm into the vessels and were secured with 4-0 silk suture. The animal was placed in the supine position, and body temperature was maintained via a heat lamp. A short piece of hypodermic tubing was inserted into the venous and arterial cannulas, and each cannula connected to a three way stopcock via a section of PE50 and 23 gauge Luer stub. The jugular line was used for administration of epinephrine and either piperoxan or phentolamine. In order to directly record arterial blood pressure, the carotid arterial line was connected to an electronic blood pressure transducer (P23db; Gould Electronics, Oxnard, Calif.). The blood pressure transducer was connected to a Gould transducer amplifier and a thermal recorder for the purpose of recording the arterial blood pressure waveform. After a stable blood pressure baseline was obtained, epinephrine was injected intravenously at a dose of 1.0 ug/kg for the purpose of inducing an alpha-adrenergic receptor mediated pressor response. This response was quantified by measurement of the arterial blood pressure waveform. After the epinephrine-induced pressor effect returned to baseline, either phentolamine or piperoxan was administered intravenously at a dose of 0.25 mg/kg. After dosing with piperoxan and phentolamine, epinephrine injections were repeated at 5, 10, 15, 20, 30, 40, 50, and 60 minutes post dosing. Arterial blood pressure was measured continuously during the length of the experiments.

Results:

Epinephrine caused a marked increase in arterial blood pressure in all rats tested. This increase was due to stimulation of vascular alpha-adrenergic receptors. Percent inhibition of the epinephrine-induced pressor effect by both phentolamine and piperoxan was used as a measure of inhibition of the alpha-adrenergic receptor. As stated previously, inhibition of the alpha receptor results in vasodilatation. Percent inhibition was calculated by the following formula:

$$\frac{(\text{Control Pressor (mmHg)} - \text{Post Test Agent Pressor (mmHg)})}{\text{Control Pressor (mmHg)}} \times 100$$

These in vivo experiments therefore describe the action of piperoxan and phentolamine as inhibitory to the pressor-induced effect of epinephrine challenge via alpha-adrenergic receptor antagonism. As shown in FIG. 1, while both agents have similar vasodilatory effects, piperoxan has a much shorter biological half-life. The estimated pharmacologic half-life of piperoxan on alpha-adrenergic receptor antagonism is approximately 30 minutes, while that of phentolamine is estimated at greater than 60 minutes. These experiments clearly establish piperoxan as an alpha-adrenergic antagonist in vivo, and with a shorter duration of action than phentolamine. Piperoxan is an agent which antagonizes sympathetically-stimulated vasoconstriction in the regulation of mammalian blood pressure, and would therefore affect the mechanistic control of penile erection through the relaxation of blood vessels of the penis. It is an agent which has a pharmacologic mechanism of action and a shorter duration of action, and therefore the occurrence of side-effects associated with the use of phentolamine, including priapism, will be reduced or entirely avoided.

EXAMPLE 2

Male New Zealand White Rabbits are anesthetized via the marginal ear vein with 25 mg/kg sodium pentobarbital.

Supplemental doses of pentobarbital are given as needed to maintain anesthesia. The rabbits are placed in a supine position and the penis is exposed. To prevent leakage of the test agent into the systemic circulation, a rubber band is placed at the base of the penis for the purpose of acting as a tourniquet. The rubber band is placed immediately before intracavernosal injection of phentolamine or piperoxan and left in place until 3 minutes after injection at which time it is removed. Piperoxan and phentolamine are dissolved in 0.9% saline and injected into the corpus cavernosa using a 27G needle. Randomly, the rabbits will receive either phentolamine or piperoxan. The initial intracavernosal injection dose will be 0.10 mg/kg for both phentolamine and piperoxan. The highest dose given will be 50 mg/kg. Following agent administration, the erection is graded for tumescence and rigidity by both palpitation and visual observance of the penis. The observations will last for up to three hours post dosing.

It is to be understood that the specific embodiments disclosed are by way of illustration, and not limitation. Various modifications may be made by one of ordinary skill siwthout departing from the scope of the invention as defined in the appended claims.

I claim:

1. A method for treating erectile impotence comprising: administering an erectile impotence relieving amount of piperoxan to a patient in need thereof.

2. The method of claim 1 wherein piperoxan is combined with a pharmaceutically acceptable carrier.

3. The method of claim 1 wherein piperoxan is selected from the group consisting of pharmaceutically acceptable acid addition salts, associated racemic mixtures and chemically pure D and L isomers thereof.

4. The method of claim 1 wherein piperoxan is combined with active agents selected from the group consisting of prostaglandins and direct vasodilators prior to administration.

5. The method of claim 4 wherein the prostaglandin is prostaglandin $E_2$ and the direct vasodilator is papaverine.

6. The method of claim 1 wherein said administration is by direct injection of between 0.25 mg/dose and 50 mg/dose piperoxan and a pharmaceutically acceptable carrier into the corpus cavernosa.

7. The method of claim 1 wherein said administration is intraurethrally via an intraurethral catheter of between 1 and 10 weight percent of piperoxan and a pharmaceutically acceptable carrier.

8. The method of claim 1 wherein said administration is topical administration directly to a penis of between 1 and 10 weight percent of piperoxan and a pharmaceutically acceptable carrier.

9. The method of claim 8 wherein said pharmaceutically acceptable carrier is hydroxypropylmethylcellulose.

10. The method of claim 1 wherein said administration is by application to a condom of between 1 and 10 weight percent of piperoxan and a pharmaceutically acceptable carrier.

11. A method of relieving erectile impotence of a human male comprising:
administering by direct injection into the corpus cavernosa of the penis of said human male between 5 mg and 25 mg of piperoxan combined with saline at a time preceding sexual engagement.

* * * * *